(12) United States Patent
Williams et al.

(10) Patent No.: US 7,071,330 B2
(45) Date of Patent: Jul. 4, 2006

(54) PROCESS FOR CARBAPENEM SYNTHESIS

(76) Inventors: John M. Williams, Merck & Co., Inc., P.O. Box 2000, Rahway, NJ (US) 07065-0907; Renato Skerlj, Merck & Co., Inc., P.O. Box 2000, Rahway, NJ (US) 07065-0907

( * ) Notice: Subject to any disclaimer, the term of this patent is extended or adjusted under 35 U.S.C. 154(b) by 219 days.

(21) Appl. No.: 10/466,876

(22) PCT Filed: Jan. 11, 2002

(86) PCT No.: PCT/US02/00821

§ 371 (c)(1),
(2), (4) Date: Jul. 16, 2003

(87) PCT Pub. No.: WO02/057266

PCT Pub. Date: Jul. 25, 2002

(65) Prior Publication Data

US 2004/0063931 A1 Apr. 1, 2004

Related U.S. Application Data

(60) Provisional application No. 60/261,933, filed on Jan. 16, 2001, provisional application No. 60/293,440, filed on May 24, 2001.

(51) Int. Cl.
*C07D 477/20* (2006.01)
(52) U.S. Cl. .................................. 540/350
(58) Field of Classification Search ............ 540/350
See application file for complete search history.

(56) References Cited

U.S. PATENT DOCUMENTS

| | | | |
|---|---|---|---|
| 3,897,424 A * | 7/1975 | Koppel et al. ............. 540/221 |
| 3,925,372 A * | 12/1975 | Chauvette ............. 540/215 |
| 3,985,737 A * | 10/1976 | Spitzer ............. 540/227 |
| 3,985,746 A * | 10/1976 | Koster et al. ............. 540/229 |
| 3,992,377 A * | 11/1976 | Chauvette et al. ............. 540/227 |
| 3,994,885 A * | 11/1976 | Koppel ............. 540/221 |
| 4,001,226 A * | 1/1977 | Spry ............. 540/215 |
| 4,217,453 A * | 8/1980 | Christensen et al. ............. 540/302 |
| 4,269,772 A | 5/1981 | Melillo et al. |
| 4,299,954 A * | 11/1981 | Spry ............. 540/230 |
| 4,369,187 A * | 1/1983 | Christensen et al. ... 514/210.09 |
| 4,383,946 A | 5/1983 | Christensen et al. |
| 4,414,155 A | 11/1983 | Liu et al. |
| 4,501,741 A * | 2/1985 | Graves et al. ............. 514/202 |
| 4,656,263 A * | 4/1987 | Kellogg ............. 540/310 |
| 4,783,453 A * | 11/1988 | Christensen et al. ... 514/210.09 |
| 5,034,384 A | 7/1991 | Greenlee et al. |
| 5,478,820 A | 12/1995 | Betts et al. |
| 5,872,250 A | 2/1999 | Williams et al. |
| 5,952,323 A | 9/1999 | Zimmerman et al. |
| 6,063,931 A | 5/2000 | Brands et al. |
| 6,180,783 B1 | 1/2001 | Williams et al. |

FOREIGN PATENT DOCUMENTS

| | | |
|---|---|---|
| EP | 0 562855 A1 | 9/1993 |
| JP | 01075488 A * | 3/1989 |
| WO | WO 974 5430 A1 | 12/1997 |

OTHER PUBLICATIONS

Kawamoto, J. Antibiotics (2001), 54(12) 1080-1092.*
D.G. Melillo et al., "A Practical Synthesis of (±)-Thienamycin", 1980, pp. 2783-27386, vol. 21, Tetrahedron Letters.
L. M. Fuentes et al., "Lewis Acid Mediated Condensation of Chiral Imide Enolates. A General Approach to the Synthesis of Chiral Carbapenem Precursors", 1985, pp. 4675-4676, vol. 108, J. Am. Chemical Society.
C. Wentrup et al., "A Stereocontrolled Synthesis of (+)-Thienamycin", 1980, pp. 6161, vol. 102, J. Am. Chemical Society.
S.M. Berge et al., "Pharmaceutical Salts", J. Pharm. Sci., vol. 66(1): pp. 1-16(1997).

* cited by examiner

*Primary Examiner*—Mark L. Berch
(74) *Attorney, Agent, or Firm*—Sylvia A. Ayler; Valerie J. Camara

(57) ABSTRACT

A process for synthesizing a compound represented by formula I:

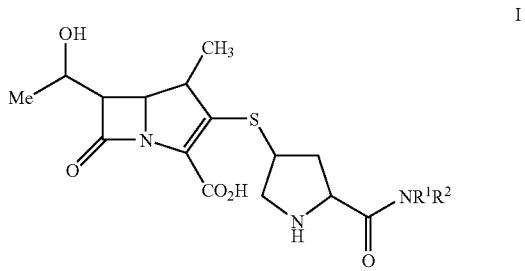

or a pharmaceutically acceptable salt thereof, wherein deprotection is conducted using a prereduced metal catalyst is disclosed.

16 Claims, No Drawings

PROCESS FOR CARBAPENEM SYNTHESIS

This application claims benefit of provisional applications 60/261,933, filed Jan. 16, 2001, and of 60/293,440, filed May 14, 2001.

BACKGROUND OF THE INVENTION

The present invention relates to a process for synthesizing carbapenem intermediates and compounds.

The carbapenems are among the most broadly effective antibiotics making them useful in the treatment of a wide range of bacterial infections. The continuing emergence of bacteria exhibiting resistance to existing therapeutic agents has made development of new carbapenems an important part of our strategy in addressing this problem.

The process developed for the manufacture of the carbapenem antibiotics disclosed herein is known to make use of a palladium-catalyzed hydrogenolysis of a p-nitrobenzyl ester. The reaction is conducted at pH 6.5 to 8.5 to minimize degradation of the product. Filtration in this pH range to remove the solid catalyst following the reaction results in a solution containing unacceptably high levels of palladium. This problem has been solved in the past by adjusting the pH to below 6 prior to filtration. This pH adjustment, however, results in degradation of the product and introduces salts, which must be removed prior to isolation of the product.

This invention relates to a process that utilizes prereduced catalysts to achieve a significantly lower level of solubilized metal derived from the catalyst following the reaction.

SUMMARY OF THE INVENTION

A process for synthesizing a compound represented by formula I:

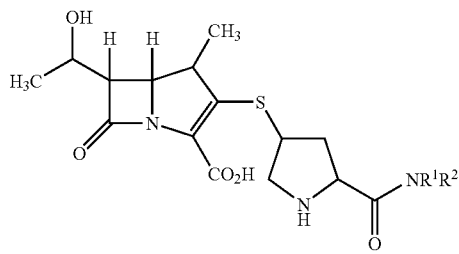

I or a pharmaceutically acceptable salt thereof, is disclosed, wherein $R^1$ and $R^2$ independently are H, $C_{1-10}$ alkyl, aryl or heteroaryl, substituted or unsubstituted, comprising deprotecting a compound of formula II:

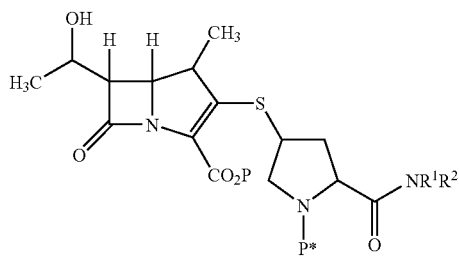

II by hydrogenolysis in the presence of a prereduced metal catalyst, purifying and isolating the compound of formula I, wherein P is a carboxyl protecting group, P* is H, $H_2^+$, or a protecting group which can be removed by hydrogenolysis such as carbobenzyloxy (CBZ), or p-nitrobenzyl carbamoyl (PNZ), and $R^1$ and $R^2$ are as described above.

These and other aspects of the invention can be realized upon complete review of the application.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight or branched, and when of sufficient size, e.g., $C_{3-15}$ may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group such as cyclopropylmethyl.

Alkyl also includes a straight or branched alkyl group which contains or is interrupted by a cycloalkylene portion. Examples include the following:

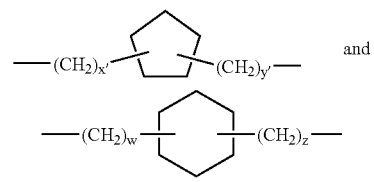

wherein: x' and y'=from 0–10; and w and z=from 0–9.

When substituted alkyl is present, this refers to a straight, branched or cyclic alkyl group as defined above, substituted with 1–3 groups as defined with respect to each variable.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one to three groups.

The term "heteroaryl" refers to a monocyclic aromatic hydrocarbon group having 5 to 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydroimidazo[4,5-c]pyridine, phthalidyl and saccharinyl, as defined below.

Substituted alkyl, aryl and heteroaryl, and the substituted portions of aralkyl, aralkoxy, heteroaralkyl, heteroaralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, aralkoxy, amino, alkylamino, dialkylamino, carboxy, trifluoromethyl and sulfonylamino.

Halo means Cl, F, Br and I selected on an independent basis.

A preferred process for synthesizing a compound represented by formula Ia:

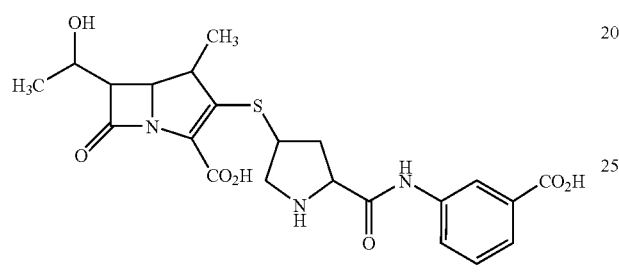

Ia or a pharmaceutically acceptable salt thereof, is disclosed, comprising deprotecting a compound of formula IIa:

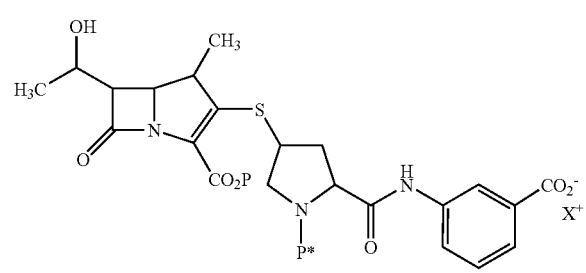

IIa by hydrogenolysis in the presence of a prereduced metal catalyst, purifying and isolating the compound of formula Ia, wherein P is a carboxyl protecting group, P* is H, $H_2^+$, or a protecting group which can be removed by hydrogenolysis such as carbobenzyloxy (CBZ), or p-nitrobenzyl carbamoyl (PNZ), and $X^+$ is a charge-balancing group. By using a prereduced catalyst, the levels of solubilized metal derived from the catalyst are significantly lower compared with the use of an unreduced catalyst. The level of solubilized metal is negligible in the sense that it is possible to isolate the compound of formula I containing pharmaceutically acceptable levels of the metal derived from the catalyst, said levels would expose a patient to no more than about 50 micrograms per day of the metal, preferably no more than 25 micrograms per day. Examples of the metal catalysts are those described herein.

In another aspect of the invention a process for synthesizing a compound represented by formula I:

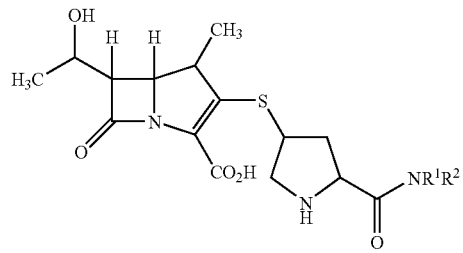

I or a pharmaceutically acceptable salt thereof, containing pharmaceutically acceptable levels of a metal derived from a metal catalyst is disclosed, wherein $R^1$ and $R^2$ independently are H, $C_{1-10}$ alkyl, aryl or heteroaryl, said alkyl, aryl or heteroaryl being substituted or unsubstituted, comprising deprotecting a compound of formula II:

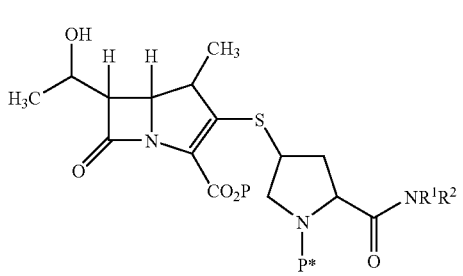

II by hydrogenolysis in the presence of a prereduced metal catalyst, purifying and isolating the compound of formula I, wherein P is a carboxyl protecting group, P* is H, $H_2^+$, or a protecting group which can be removed by hydrogenolysis, and $R^1$ and $R^2$ are as described above. A preferred aspect of this process is realized when it is conducted with a compound of formula IIa to produce a compound of formula Ia.

The compounds of formula I and Ia' can be obtained as shown below in Flow Sheets A-1 and A-2, respectively.

FLOW SHEET A-1

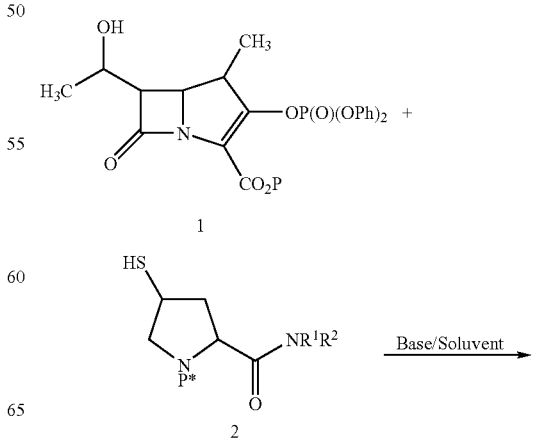

-continued

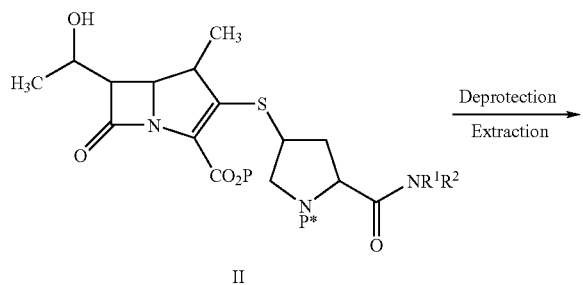

II

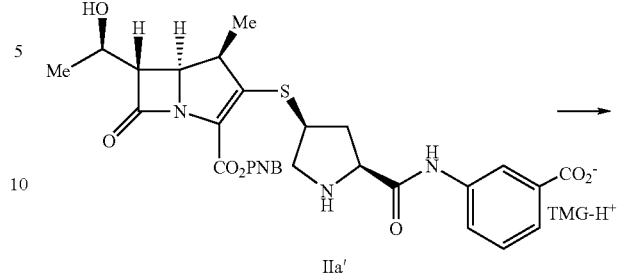

IIa'

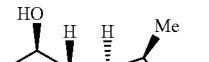

3a

3

1

Flow sheet A-2 below provides a preferred process as it relates to 1β-methylcarbapenems.

FLOW SHEET A-2

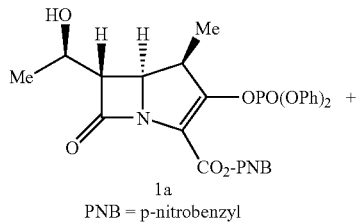

1a
PNB = p-nitrobenzyl

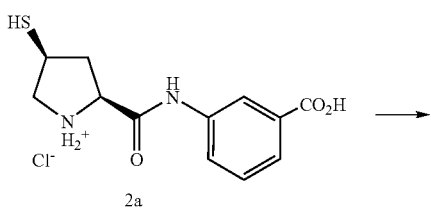

2a

Compounds 1, 1a, 2 and 2a can be obtained in accordance with techniques such as those disclosed in U.S. Pat. No. 5,034,384, granted on Jul. 23, 1991; U.S. Pat. No. 5,952,323, granted on Sep. 14, 1999; U.S. Pat. No. 4,994,568 granted on Feb. 19, 1991; U.S. Pat. No. 4,269,772 granted on May 26, 1981; U.S. Pat. No. 4,350,631 granted on Sep. 21, 1982; U.S. Pat. No. 4,383,946 granted on May 17, 1983; U.S. Pat. No. 4,414,155 granted on Nov. 8, 1983; U.S. Pat. No. 6,063,931, granted May 16, 2000; EP-A-562855; *Tetrahedron Lett.* 21, 2783 (1980); *J. Am. Chem. Soc.* 102, 6161 (1980); *J. Am. Chem. Soc.* 108, 4675 (1986) and U.S. Pat. No. 5,478,820 granted on Dec. 26, 1995. The teachings of these references are incorporated herein by reference. Compounds of formula I and Ia and derivatives thereof and processes thereof are disclosed in U.S. Pat. No. 5,872,250, granted Feb. 16, 1999 and U.S. Pat. No. 6,180,783, granted Jan. 30, 2001, both incorporated herein by reference.

The compounds of formula II or IIa' or salts thereof are produced by reacting the enol phosphate 1 or 1a and thiol 2 or 2a in the presence of a base. This reaction is typically conducted at reduced temperature, e.g., about −30° C. to about −70° C., preferably about −40° C. to about −60° C. Bases which are suitable for the above reaction include organic as well as inorganic bases. Preferred bases for use herein are secondary and tertiary amines such as diisopropylamine (DIPA), dicyclohexylamine (DCHA), 2,2,6,6-tetramethylpiperidine (TMP), guanidines such as 1,1,3,3-tetramethylguanidine (TMG), N,N,N',N'N'''-tetraethylcyclohexylguanidine (TECHG), N,N',N'',N'''-dicyclohexyldiethylguanidine (DCDEG) and amidines such as 1,8-diazabicyclo[4.3.0]undec-7-ene (DBU) and 1,5-diazabicyclo [4.3.0] non-5-ene (DBN). Most preferable bases are the guanidine bases and even more preferred is TMG.

An antioxidant is optionally added. Preferred antioxidants are $PR_3$, wherein $R_3$ belongs to the group consisting of $C_{1-8}$ alkyl, aryl or heteroaryl, or aromatic phenols such as BHT (butylated hydroxy toluene) and BHA (butylated hydroxy anisole). Most preferred antioxidant is $PBu_3$.

The reaction can be conducted in a polar organic solvent, e.g., N-ethylpyrrolidinone NEP), N-methylpyrrolidinone, N,N-dimethylformamide (DMF), N,N-dimethylacetamide (DMA), acetonitrile, propionitrile, or a mixture thereof and the like. The preferred solvent is N-ethylpyrrolidinone (NEP).

After coupling, the carbapenem can be stabilized by combining the carbapenem with a carbon dioxide source. Stabilization can be conducted according to the teachings in U.S. Pat. No. 6,180,783, granted Jan. 30, 2001 and incorporated by reference herein.

The carbapenem is subjected to deprotection, thus removing the 3-carboxyl protecting group yielding I or Ia'.

In the claimed invention, hydrogenolysis is conducted in the presence of a prereduced metal catalyst. The preferred reaction involves $H_2$ gas with a prereduced palladium (Pd on carbon) catalyst. The reaction can be conducted under hydrogen over a broad pressure range, preferably above 40 psi. A base such as sodium hydroxide or sodium bicarbonate can be added during the reaction to control pH. Sufficient sodium bicarbonate can be present at the start of the reaction to control the pH. Preferably, the reaction is conducted in the presence of a source of carbon dioxide such as sodium bicarbonate to give the stabilized form 3 or 3a where $X^+$ is a charge-balancing group.

Suitable catalysts are those which contain a metal known to be useful for catalytic hydrogenation such as palladium (Pd), platinum (Pt), and rhodium (Rh), preferably Pd. The metal catalyst can be a salt or metal powder or supported on a wide range of solid supports known to be useful in catalytic hydrogenation reactions including alumina, silica, calcium carbonate, barium carbonate, barium sulfate, strontium carbonate, polymers, or carbon, preferably activated carbon. The catalyst is used in an amount that is at least 5 mol % relative to the carbapenem substrate. A pre-reduced catalyst is formed by chemical treatment with a reducing agent prior to addition of the substrate. Suitable reducing agents include those known to be useful for the reduction of metal catalysts such as formate, borohydride, and hydrogen, preferably hydrogen. The reduction can be performed in manufacture of the catalyst or just prior to use. The pH can be controlled during reduction by addition of a base. Preferred bases are sodium hydroxide or sodium bicarbonate.

Carbon dioxide sources, as used herein, refer to carbon dioxide gas as well as compounds which can produce carbon dioxide in solution. Representative examples include carbonates and bicarbonates, such as sodium carbonate, sodium bicarbonate, potassium carbonate and potassium bicarbonate. Preferably, the carbon dioxide source is sodium bicarbonate. The sodium bicarbonate can be purchased or obtained by mixing sodium hydroxide and carbon dioxide at a pH above about 6.5. The carbon dioxide source can alternatively be included in the reaction medium prior to or added during the deprotection reaction.

Examples of suitable 3-carboxyl protecting groups are those which can be removed by hydrogenolysis. Examples of such protecting groups are: benzhydryl, o-nitrobenzyl, p-nitrobenzyl, 2-naphthylmethyl, and benzyl. A preferred carboxyl protecting group is p-nitrobenzyl (PNB). Many other suitable protecting groups are known in the art. See, e.g., T. W. Greene, *Protective Groups in Organic Synthesis*, John Wiley & Sons, Inc., 1981 (Chapters 2 and 5).

Numerous salt-forming ions are recited in Berge, S. M., et al. J. Pharm. Sci. 66(1): 1–16 (1977), the teachings of which are incorporated herein by reference. The charge balancing group $X^+$ maintains overall charge neutrality. Preferably $X^+$ represents a pharmaceutically acceptable salt-forming cation. Preferred salt-forming cations are selected from the group consisting of: sodium, potassium, calcium and magnesium. More preferably the salt-forming cation is a member selected from the group consisting of: $Na^+$, $Ca^{+2}$ and $K^+$.

The salt-forming cations mentioned above provide electronic balance and overall charge neutrality. From zero to three positively charged counterions may be present depending upon the number of charged moieties on the carbapenem. The number of negatively charge groups is largely a function of pH, since these groups become protonated as the pH is lowered. For every positively charged functional group on the molecule, a negatively charged counterion is present to provide overall charge neutrality. Different counterions may also be included in the overall reaction composition. Hence, for example, calcium and sodium could be included together in the reaction to provide overall charge neutrality. The counterions can thus be varied within wide limits. Generally, the counterion or counterions are pharmaceutically acceptable cationic species.

The compounds formed in the present invention have asymmetric centers and occur as racemates, racemic mixtures, and as individual diastereomers. The processes of synthesizing all such isomers, including optical isomers, are included in the present invention.

Purification and isolation of compounds of formula I and Ia can be achieved via a combination of several operations: extractions using solvents such as dichloromethane to remove residual organic solvents, chromatography using hydrophobic resin chromatography (eluting with 0.05 M sodium bicarbonate at about 5° C.), nanofiltration for concentration of the process stream followed by crystallization of the pure drug (See U.S. Ser. No. 09/093813, filed Jun. 9, 1998, incorporated herein by reference).

Alternatively, the column chromatography and nanofiltration operations can be eliminated when the extraction is carried out with an appropriate alcohol. A preferred extraction is carried out with the appropriate alcohol in the presence of an ion-pairing reagent. The process described below allows a direct crystallization of carbapenem compounds after this type of extraction.

The extractions can be conducted by methods generally known in the art. A preferred extraction process is discussed in U.S. Ser. No. 09/487,044 filed Jan. 19, 2000, which is incorporated herein by reference. An example of the extraction involves extracting a solution containing a compound of formula I, Ia, 3, or 3a, or a pharmaceutically acceptable salt thereof, wherein each $X^+$ is a charge-balancing group and is present or absent as necessary to provide overall charge neutrality, with an alcohol, crystallizing and collecting a compound of formula I or Ia' from the resultant aqueous phase. It is preferable that the extraction is conducted in the presence of an ion-pairing reagent and that pH of the aqueous phase is maintained between neutral and mildly basic pH (pH 7 to 9) according to the teachings of WO 9745430. It is also preferable that the extraction is performed while I or Ia is stabilized in the form, 3 or 3a. After extraction, the stabilized form 3 or 3a is readily converted to a salt form of I or Ia under neutral to mildly acidic conditions (pH 7 to 5). The pH is adjusted to produce the appropriate salt form of I or Ia for isolation by crystallization. Alternatively, there can be multiple extractions with, for example the example solvents being isoamyl alcohol (IAA)/DPP solution in the first extraction, and IAA in a second extraction.

It is preferable to use equipment that is capable of multi-stage extraction such as mixer-settler cascade, spray tower, baffle tower, packed tower, perforated plate tower, mechanically agitated extractor, pulsed extractor, reciprocating plate extractor, or centrifugal extractor for optimal performance. Most preferable is the use of a multi-stage centrifugal extractor. The preferred equipment is dependent on scale; CINC (Costner Industries Nevada Corporation) liquid-liquid centrifugal separators are preferred for laboratory scale operation; whereas, a Podbielniak® centrifugal extractor is preferred for large scale operation.

Use of these multi-stage centrifugal extractor provides unexpected benefits. For example, the ion pairing reaction of TMG with diphenyl phosphate (DPP) is used to reduce the TMG level in the process stream prior to the isolation of the compound of formula I, Ia, 3 or 3a. In addition to this purification, the residual reaction solvent, N-ethyl pyrrolidinone (NEP) must be removed from the process stream, and the process stream must be concentrated four fold to allow successful crystallization of the compound of formula I, Ia, 3 or 3a. All three of these processing requirements are accomplished simultaneously via a rapid, multi-stage, counter-current centrifugal extraction, which minimizes the soluble product degradation during processing.

The alcohol useful for the present invention includes but is not limited to iso-amyl alcohol, tert-amyl alcohol, 1-butanol, 2-butanol, 1-octanol, 1-hexanol, 1-heptanol, cyclohexanol, 1-pentanol, cyclopentanol, 2-pentanol, 2-methyl-1-pentanol, 2-ethyl-1-butanol, 4-methyl-2-pentanol, 2,6-dimethyl-4-heptanol, 2-methylcyclohexanol, preferably 1-butanol or iso-amyl alcohol.

Preferred ion-pairing reagents for use in the present invention are $C_{6-24}$ carboxylic acids, phosphoric acids, phosphinic acids, sulfonic acids and the like and their salts. Most preferred ion-pairing reagents are the sodium salts of diphenylphosphoric acid, stearic acid or dodecylbenzenesulfonic acid.

EXAMPLE

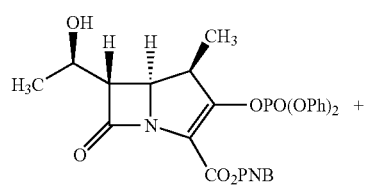

PNB = p-nitrobenzyl

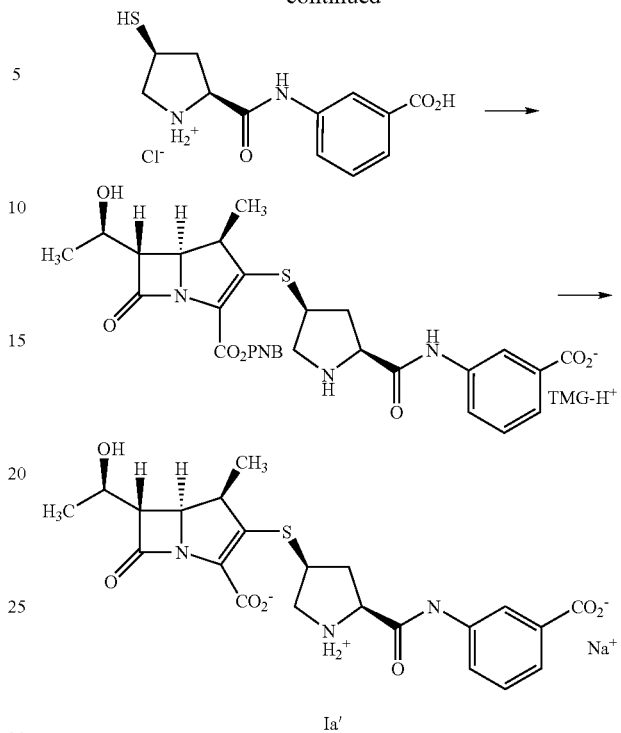

Ia'

A hydrogenator is charged with 63 g of 10% Pd on carbon catalyst (dry weight) in 1.8 L of water. The vessel is placed under hydrogen then vented and placed under nitrogen. Sodium hydroxide (68 g, 50%) is charged adjusting the pH to about 7.5 with carbon dioxide.

The enol phosphate (170 g) and the thiol (86 g) are dissolved in 1.3 L of N-ethylpyrrolidinone (NEP). The mixture is cooled to below −40° C. and 1,1,3,3-tetramethylguanidine (109 g) is added. After 3 hours, the reaction mixture is quenched into the hydrogenator at below 15° C. adjusting the pH to about 8 with carbon dioxide. The vessel is placed under hydrogen. When the reaction is complete, the hydrogen is vented and the reaction mixture is treated with activated carbon and filtered. The filtrate is extracted with iso-amyl alcohol containing diphenylphosphoric acid (240 g) and 50% NaOH (44 g). The resulting aqueous solution is further extracted with iso-amyl alcohol to give an aqueous solution containing at least 90 mg/mL of the product. Both extractions are performed using two CINC centrifugal separators set in series for countercurrent extraction. The pH is adjusted to 5.5 with acetic acid. The product is crystallized by adding equal volumes of methanol and 1-propanol at below −5° C. and isolated by filtration. The solid is washed with a mixture of 2-propanol and water (85:15 v/v) then dried to yield a compound of formula Ia'.

While certain preferred embodiments of the invention have been described herein in detail, numerous alternative embodiments are contemplated as falling within the scope of the appended claims. Consequently the invention is not to be limited thereby.

What is claimed is:

1. A process for synthesizing a compound represented by formula I:

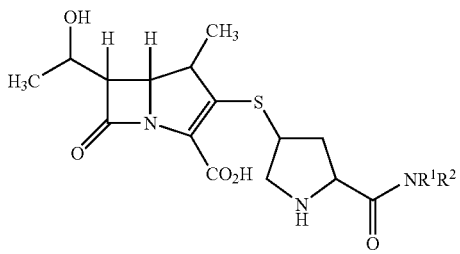

or a pharmaceutically acceptable salt thereof, wherein $R^1$ and $R^2$ independently are H, $C_{1-10}$ alkyl, aryl or heteroaryl, said alkyl, aryl or heteroaryl being substituted or unsubstituted, comprising deprotecting a compound of formula II:

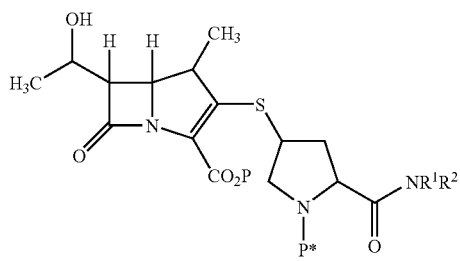

by hydrogenolysis in the presence of a prereduced metal catalyst belonging to the group consisting of palladium, platinum and rhodium, and a base to give a solution of formula I, extracting a solution containing a compound of formula I or 3.

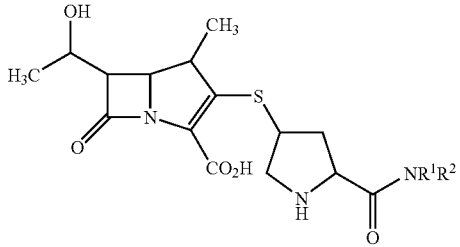

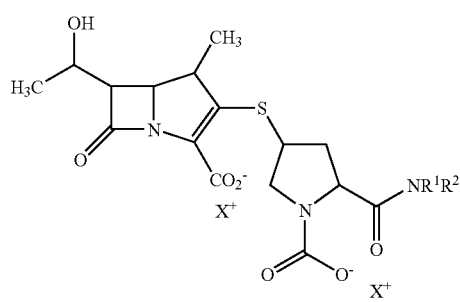

or a pharmaceutically acceptable salt thereof, wherein each $X^+$ is a charge-balancing group, and $R^1$ and $R^2$ are as described above with a $C_{4-10}$ alcohol in the presence of an ion-pairing reagent, while maintaining a pH of the aqueous phase between neutral and mildly basic, and isolating the compound of formula I or 3 from the resulting aqueous phase, wherein the metal catalyst is a salt or metal powder or supported on solid supports selected from the group consisting of alumina, silica, calcium carbonate, barium carbonate, barium sulfate, strontium carbonate, polymers, or carbon, P is a carboxyl protecting group which can removed by hydrogenolysis, P* is H, $H_2^+$, or a protecting group which can be removed by hydrogenolysis, wherein when P* is $H_2^+$ a negatively charged counterion is present.

2. A process according to claim 1 wherein the extraction is conducted using a multi-stage extractor.

3. A process according to claim 2 wherein the extraction is conducted using a multi-stage countercurrent centrifugal extractor.

4. A process in accordance with claim 1 wherein the alcohol is iso-amyl alcohol, tert-amyl alcohol, 1-butanol, 2-butanol, 1-octanol, 1-hexanol, 1-heptanol, cyclohexanol, 1-pentanol, cyclopentanol, 2-pentanol, 2-menthyl-1-pentanol, 2-ethyl-1-butanol, 4-methyl-2-pentanol, 2,6-dimethyl-4-heptanol, or 2-methylcyclohexanol and the metal catalyst is prereduced palladium on carbon.

5. A process in accordance with claim 4 wherein the alcohol is iso-amyl alcohol or 1-butanol.

6. A process in accordance with claim 1 wherein the ion-pairing reagent comprises $C_{6-24}$ carboxylic acids, phosphoric acids, phosphinic acids, sulfonic acids or their salts.

7. A process in accordance with claim 5 wherein ion-pairing reagent is a sodium salt of diphenylphosphoric acid, stearic acid or dodecylbenzenesulfonic acid.

8. A process according to claim 1 wherein the extracted solution contains a compound of formula 3.

9. A process for synthesizing a compound represented by formula Ia:

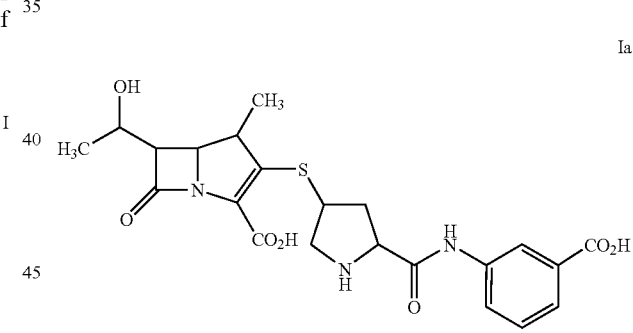

or a pharmaceutically acceptable salt thereof, is disclosed comprising deprotecting a compound of formula IIa:

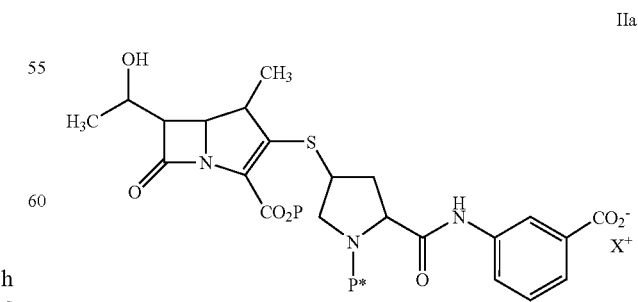

by hydrogenolysis in the presence of a prereduceed metal ctalyst beloning to the group consisting of palladium, platinum and rhodium, and base to give a solution of formula Ia, extracting a solution containing a compound of formula Ia or 3a:

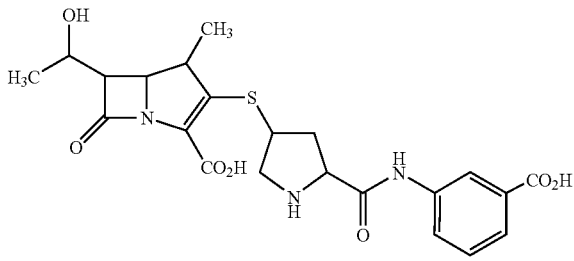

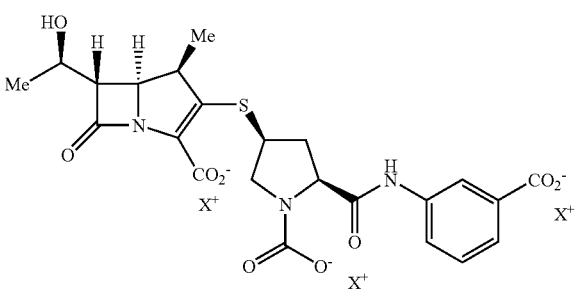

or a pharmaceutically acceptable salt thereof, wherein each $X^+$ is a charge-balancing group, with a $C_{4-10}$ alcohol in the presence of an ion-pairing reagent, while maintaining a pH of the aqueous phase between neutral and mildly basic, and isolating the compound of formula Ia from the resulting agueous phase, wherein the metal catalyst is a salt or metal powder or supported on solid supports selected from the group consisting of alumina, silica, calcium carbonate, barium carbonate, barium sulfate, strontium carbonate, polymers, or carbon, P is a carboxyl protecting group which can removed by hydrogenolysis, P* is H, $H_2^+$, or a protecting group which can be removed by hydrogenolysis, wherein when P* is $H_2^+$ a negatively charged counterion is present.

10. A process according to claim 9 wherein the extraction is conducted using a multi-stage extractor.

11. A process according to claim 10 wherein the extraction is conducted using a multi-stage countercurrent centrifugal extractor.

12. A process in accordance with claim 9 wherein the alcohol is iso-amyl alcohol, tert-amyl alcohol, 1-butanol, 2-butanol, 1-octanol, 1-hexanol, 1-heptanol, cyclohexanol, 1-pentanol, cyclopentanol, 2-pentanol, 2-methyl-1-pentanol, 2-ethyl-1-butanol, 4-methyl-2-pentanol, 2,6-dimethyl-4-heptanol, or 2-methylcyclohexanol and the metal catalyst is prereduced palladium on carbon.

13. A process in accordance with claim 12 wherein the alcohol is iso-amyl alcohol or 1-butanol.

14. A process in accordance with claim 9 wherein the ion-pairing reagent comprises $C_{6-24}$ carboxylic acids, phosphoric acids, phosphinic acids, sulfonic acids or their salts.

15. A process in accordance with claim 14 wherein the ion-pairing reagent is a sodium salt of diphenyiphosphoric acid, stearic acid or dodecylbenzenesulfonic acid.

16. A process according to claim 9 wherein the extracted solution contains a compound of formula 3a:

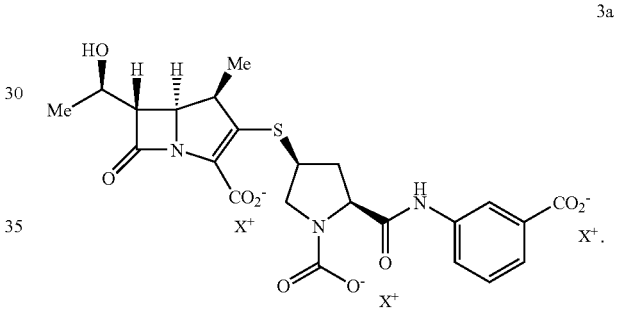

* * * * *